United States Patent
Addiego et al.

(10) Patent No.: US 6,623,707 B1
(45) Date of Patent: Sep. 23, 2003

(54) MONOLITHIC CATALYST DEHYDROGENATION REACTOR

(75) Inventors: William P. Addiego, Big Flats, NY (US); Stephen A. Campbell, Corning, NY (US); Wei Liu, Painted Post, NY (US); Mitchell E. Odinak, Horseheads, NY (US)

(73) Assignee: Corning Incorporated, Corning, NY (US)

(*) Notice: Subject to any disclaimer, the term of this patent is extended or adjusted under 35 U.S.C. 154(b) by 490 days.

(21) Appl. No.: 09/597,888

(22) Filed: Jun. 19, 2000

(51) Int. Cl.[7] .............................. C07C 5/32; C07C 5/33; B01J 8/02; B01J 8/04; B01J 35/02

(52) U.S. Cl. ...................... 422/190; 422/188; 422/191; 422/192; 422/198; 422/199; 422/211; 422/190; 422/218; 422/222; 585/440

(58) Field of Search ................................. 422/187, 188, 422/190, 192, 198, 200, 211, 189, 191, 193, 218, 222, 199; 585/440

(56) References Cited

U.S. PATENT DOCUMENTS

| | | | | |
|---|---|---|---|---|
| 4,039,602 | A | 8/1977 | Uitti | 585/441 |
| 4,347,396 | A | 8/1982 | Takano et al. | 585/441 |
| 4,711,930 | A | 12/1987 | Hoelderich et al. | 502/445 |
| 4,720,604 | A | 1/1988 | Chu | 585/445 |
| 4,774,378 | A | 9/1988 | Faure et al. | 585/441 |
| 4,914,249 | A | 4/1990 | Benedict | 585/443 |
| 5,023,225 | A | 6/1991 | Williams et al. | 502/304 |
| 5,053,572 | A | 10/1991 | Kim et al. | 585/441 |
| 5,097,091 | A | 3/1992 | Kremer et al. | 585/444 |
| 5,171,914 | A | 12/1992 | Hamilton, Jr. | 585/444 |
| 5,358,698 | A | 10/1994 | Butler et al. | 422/218 |
| 5,679,878 | A | 10/1997 | Chen et al. | 585/444 |
| 5,710,356 | A | 1/1998 | Subramaniam et al. | 585/440 |
| 5,733,518 | A | 3/1998 | Durante et al. | 423/248 |
| 5,856,605 | A | 1/1999 | Deimling et al. | 585/440 |
| 6,177,382 | B1 * | 1/2001 | Hesse et al. | 502/439 |
| 6,440,885 | B1 * | 8/2002 | Pierotti et al. | 502/4 |
| 6,452,061 | B1 * | 9/2002 | Schmidt et al. | 585/658 |

* cited by examiner

Primary Examiner—Jerry D. Johnson
Assistant Examiner—Alexa J. Doroshenk
(74) Attorney, Agent, or Firm—Kees van der Sterre

(57) ABSTRACT

Axial flow dehydrogenation reactors comprising multiple catalyst beds formed of honeycomb monoliths, the beds being separated from each other by heating stages to maintain reactant stream temperature, provide low pressure drop and improved conversion efficiency when used alone or in combination with other reactors, e.g., as reactor upgrades for series reactor systems incorporating radial flow reactor stages.

27 Claims, 2 Drawing Sheets

MONOLITHIC CATALYST DEHYDROGENATION REACTOR

BACKGROUND OF THE INVENTION

The present invention relates to catalytic reactors for carrying out dehydrogenation reactions, and has particular application to reactors for the dehydrogenation of ethylbenzene to produce styrene.

A well-known process for the commercial production of styrene via the dehydrogenation of ethylbenzene involves combining ethylbenzene with steam to form a diluted feed stream which is then further heated to a suitable reaction temperature (e.g., 500–700° C.) in a preheating furnace. The pre-heated feed stream is then fed at low pressure into a catalytic reactor typically containing a bed of iron oxide-based catalyst pellets. The dehydrogenation reaction to produce styrene is endothermic, with styrene yields being favored at relatively high temperatures and low pressures.

The complex product of the dehydrogenation reaction generally comprises a vaporized mixture of styrene and unreacted ethylbenzene together with water vapor, $H_2$, CO, $CO_2$, light hydrocarbons, benzene, toluene, and heavier components such as polymerized by-products. The vapor mixture is cooled to condense and separate the liquid phase from the gas phase, and the separated liquid is processed through a series of distillation columns to recover the styrene and recycle the unreacted ethylbenzene.

Commercial styrene production typically involves processing the ethylbenzene through two or more catalytic reactor stages operating in series, with the feed stream being reheated between stages to compensate for the heat lost during the endothermic process. U.S. Pat. No. 4,347,396 discloses a processing system incorporating a series of reactors for this purpose.

Since the equilibrium constant for ethylbenzene-to-styrene conversion depends inversely on reactor pressure, pressure drops within commercial reactors are kept as low as possible. A high catalyst surface area:volume ratio increases mass transfer efficiency and suppresses undesirable by-product formation. Catalyst utilization and efficiency can be improved somewhat by using tightly packed beds of relatively small catalyst beads or pellets, but such use increases reactor pressure drop, tending to negate the expected improvements in catalytic conversion rate and styrene selectivity.

One way to address the pressure drop problem is to deploy the packed pellet beds in a radial flow reactor. One example of such a reactor is disclosed in U.S. Pat. No. 5,358,698. Compared to the pressure drops developed by unidirectional feed stream flows across conventional packed catalyst beds, radial flow reactors significantly reduce pressure drop by dispersing the catalyst beads around a large cylindrical volume encircling the feed stream inlet. At the same time, the gas linear velocity through the distributed pellet bed is reduced.

Unfortunately, however, several drawbacks associated with radial flow reactors remain. Among these are the fact that the gas distribution and collection chambers for these reactors take up a large fraction (30–60%) of the overall volume of the reactor. Thus, the space utilization efficiency of radial reactors is low.

In addition, radial reactor designs require that the feed stream change flow direction at least twice between the gas inlet and gas outlet of the reactor. This kind of flow pattern can cause poor gas distribution over the packed bed along the reactor axis that can reduce catalyst efficiency, and can increase catalyst attrition along the edges of the cylindrical beds. Extra catalyst bed support structures and screening are also required, increasing the capital cost of the reactor and introducing operating reliability issues.

Finally, it is more difficult and expensive to introduce heat uniformly into the middle of the catalyst bed in these reactors. Thus larger temperature gradients tend to develop within the catalyst bed that negatively affect conversion, selectivity, and catalyst stability.

Honeycomb monolithic catalysts such as disclosed in U.S. Pat. No. 4,711,930 have been considered for use in dehydrogenation reactions but have found little use in commercial chemical processing systems. In principle, these catalysts should offer reduced feed stream pressure drops and improved heat/mass transfer efficiency when compared with pelletized catalysts. However, the art has not yet developed dehydrogenation reactor designs that effectively exploit the performance characteristics of these catalysts.

SUMMARY OF THE INVENTION

The present invention provides axial flow reactor designs offering efficiencies higher than those of existing pellet bed and radial flow reactors, while at the same time maintaining or reducing reactor size and capital cost. The designs can be employed in standalone systems, or they can be used for retrofit or supplemental reactors that can significantly improve the efficiency of existing series reactor systems.

The improved reactor designs of the invention include an improved axial flow dehydrogenation reactor that effectively exploits the advantages of honeycomb catalyst packing (hereinafter also referred to as monolithic packing). The reactor assembly includes a reaction chamber having an inlet and an outlet and containing two or more beds of monolithic catalyst disposed therewithin. The catalyst beds include an upstream bed and a downstream bed disposed in series along the reactant flowpath, the latter generally following a flow axis traversing the chamber from an upstream to a downstream direction between the chamber inlet and outlet.

Each of the catalyst beds in the chamber is formed of one or more monolithic dehydrogenation catalysts, each of which is a honeycomb catalyst incorporating a plurality of open-ended honeycomb channels traversing the catalyst from the upstream to the downstream direction on the reactant flowpath. These channels provide catalytically active channel wall surfaces for treating a heated vapor stream containing a hydrogen-containing reactant passing through the catalyst bed, at least partially converting the reactant to a dehydrogenated product in an efficient manner and at low pressure drops.

Also disposed within the chamber, and situated between the upstream and downstream catalyst beds to separate them from one another, are heating means for re-heating the vapor stream after traversal of the upstream catalyst bed. The heating means, which are preferably also designed to operate a low pressure drop, provide an effective and space-efficient way to restore heat energy to the reactant stream prior to its traversal of the downstream reactor bed.

Reactors of the described type may be utilized alone or in series to carry out a variety of endothermic dehydrogenation reactions at conversion rates equivalent or better than achievable in packed bed reactor systems. However, an alternative and preferred use of such a reactor is in combination with a radial flow reactor in a multiple-stage dehydrogenation reactor systems for the conversion of ethylbenzene to styrene. By a multiple-stage reactor system is meant a reactor system incorporating two or more dehydrogenation reactors in series, each reactor constituting a stage in the dehydrogenation process.

In another aspect the invention includes a multiple-stage dehydrogenation reactor system comprising at least two reactors in series. The system includes an axial flow reactor stage connected with a second reactor stage, the second stage being a second axial flow reactor stage or, more typically, a radial flow reactor stage.

The axial-flow reactor stage comprises a first reaction chamber having a first inlet and a first outlet and containing at least one monolithic catalyst bed of the kind above described, i.e., incorporating one or more monolithic honeycomb catalysts, each of which has honeycomb channels disposed along the flow axis within the chamber. More preferably, the axial flow stage will include at least two monolithic catalyst beds separated by heating means as above described, the upstream bed and downstream bed again being disposed in series along the flow axis and the heating means operating to add heat to reactant stream under endothermic reaction conditions.

Where a radial flow reactor stage is used as the second stage in the dehydrogenation reactor system, the radial stage may be of conventional design. Typically, it will include a second reaction chamber having a second inlet and a second outlet wherein the inlet is connected directly or indirectly to the outlet of the first reaction chamber or axial flow reactor stage.

Included within the second reaction chamber in the case of a radial flow reactor are a central inlet section for collecting the reactant stream entering the chamber through the inlet, a radial flow catalyst bed distributed about and encircling the inlet section for treating the reactant stream collecting in the inlet section, and a surrounding outlet section for collecting the product stream produced by passage of the reactant stream through the catalyst bed.

As in most radial reactor designs, the outlet section is a peripheral or circumferential volume occupying the space between the catalyst bed and the chamber wall, within which section the product stream may be collected as it flows radially outwardly through the distributed catalyst bed. The outlet section connects with the chamber outlet from which the collected product stream is discharged from the reactor.

Whether or not heating means are provided within the axial flow reactor stage in such a reactor, most two-stage reactor designs will include some inter-stage heating means for adding heat to the reactant stream. Such heating means will be disposed downstream of the monolithic catalyst bed(s) present in the axial reactor stage and upstream of the radial catalyst bed. In case of lack of space in the radial flow reactor chamber, such heating means may be positioned between the outlet of the axial stage and the inlet of radial stage, More typically, however, it is incorporated as part of the radial flow reactor at the inlet end thereof. In either case the heating means will be sufficient in capacity to reheat the cooled reactant stream issuing from the outlet of the axial stage prior to delivering it to the catalyst bed within the radial flow reactor.

The invention further comprises a method for treating a reactant stream to at least partially dehydrogenate a hydrogen-containing reactant present therein. In accordance with that method the reactant stream is heated to a first dehydrogenation reaction temperature and is then conveyed through a first dehydrogenation reactor containing at least one catalyst bed of monolithic honeycomb dehydrogenation catalysts. This step of the method effects dehydrogenation of at least a portion of the reactant to produce a partially dehydrogenated intermediate stream.

Thereafter the intermediate stream is heated to a second dehydrogenation reaction temperature and is conveyed through a second dehydrogenation reactor containing at least one bed of a second dehydrogenation catalyst. This step effects a further dehydrogenation of the intermediate stream to produce a dehydrogenated product stream.

The second dehydrogenation catalyst can be a monolithic dehydrogenation catalyst of honeycomb shape, or it can be another low-pressure-drop dehydrogenation catalyst bed. In the latter case the low pressure drop catalyst bed will typically be a short path length bed made up of a granular, beaded, or pelletized dehydrogenation catalyst, such as the shallow catalyst bed of a radial flow dehydrogenation reactor.

The enhanced reactor productivity and conversion efficiency of the monolithic catalyst reactors of the present invention improve dehydrogenation performance in a number of ways. For example, the difficulties of separating dehydrogenated product from feed, including the separations required in the ethylbenzene/styrene conversion process, are well known. The reactors of the invention alleviate these difficulties through higher one-pass dehydrogenation conversions at the same or higher capacities, resulting in substantial savings in downstream separation costs and the costs of recycling unreacted.

Another benefit of using monolithic reactors is that the dehydrogenation process can be conducted under less severe reaction conditions, e.g., at reduced temperatures. Such conditions prolong catalyst lifetime and further reduces operating costs.

BRIEF DESCRIPTION OF DRAWINGS

The invention may be further understood by reference to the drawings, wherein.

DETAILED DESCRIPTION

Figure 1:
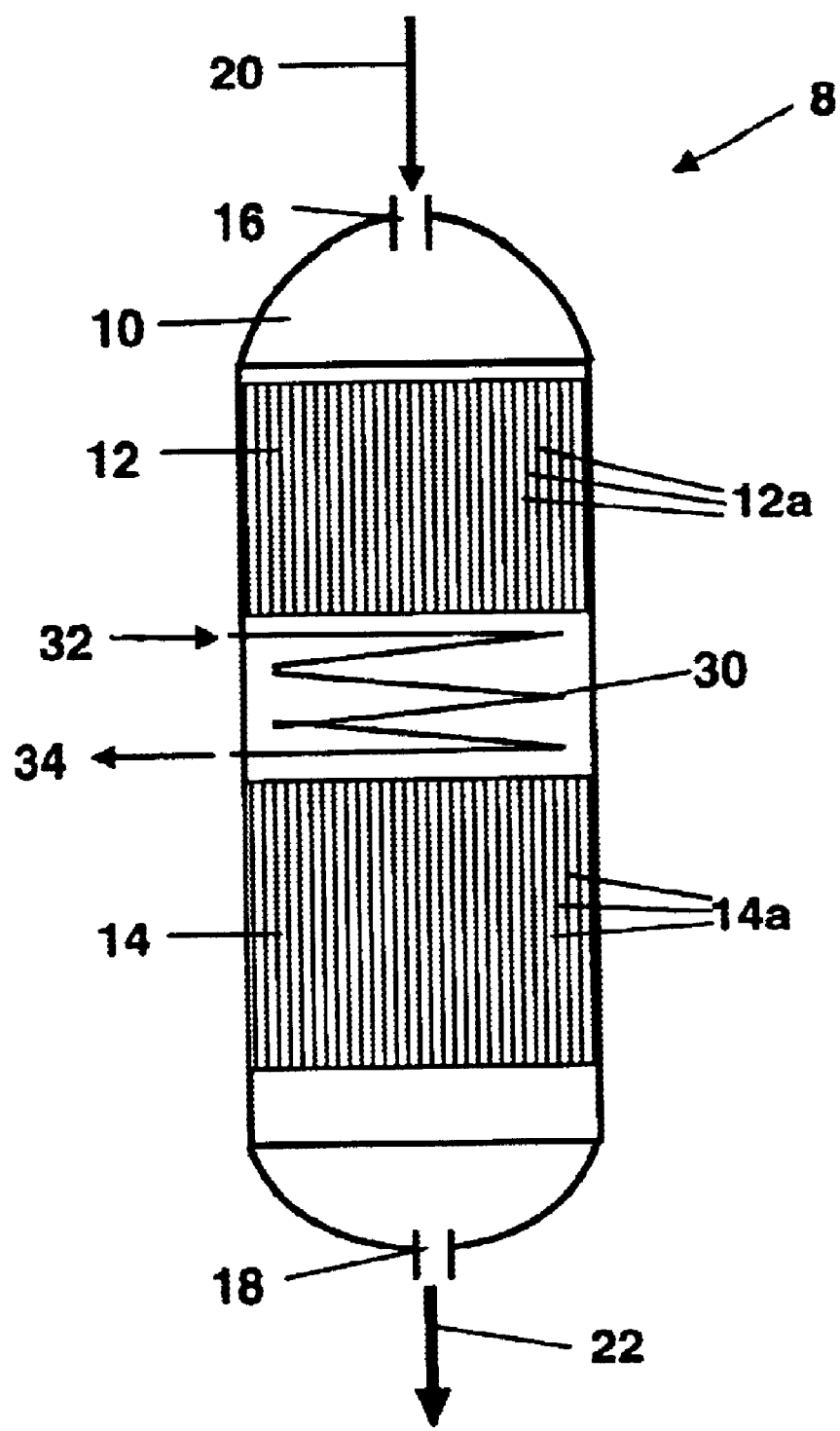
FIG. 1 is a schematic elevational view of a dehydrogenation reactor provided with honeycomb monolithic catalyst in accordance with the invention.

Although the present invention is generally useful for the design of reactors for a variety of dehydrogenation reactions of alkyl aromatics and other compounds, it has particular application for highly endothermic reactions such as the production of styrene by the dehydrogenation of ethylbenzene. The following description and examples therefore may refer specifically to styrene production even though the invention has application to other dehydrogenation reactions in the field.

While it is generally understood that equilibrium in dehydrogenation reactions favors product formation at lower reaction pressures, the effects of reactor pressure drop on the conversion of ethylbenzene to styrene have not been thoroughly studied in the literature. However, isothermal reactor simulations run at constant reactor exit pressure and $H_2O$/ethylbenzene feed ratio predict a steady decrease in ethylbenzene conversion as the reactor pressure drop is raised. For example, a 1.1 bar increase in reactor pressure drop would be effective to cause a decrease of about 10% in the conversion of ethylbenzene, a significant decrease for a commercial process. Monolithic reactor packings offer the possibility of lower pressure drops and more uniform pressures throughout the catalyst bed than either radial flow or packed bed axial flow reactors. Also, the low flow resistance of monolith reactors means that substantial increases in diluent flow (e.g. steam) into the feed stream can be tolerated without raising the pressure drop across the packing to harmful levels. As is known, the beneficial effect of such dilution is to significantly increase the equilibrium conversion limit to styrene.

Reactor dimensions useful in securing the advantages of monolithic honeycomb catalysts in dehydrogenation reactions of the kind described will depend in part on the number of catalyst beds to be included in the reactor and the sizes of the beds employed. However, over a relatively broad range of reactor capacities it will be found that ratios of reactor length to reactor volume in the range of about 1:1 up to about 1:30 will generally be observed.

Yet another important advantage monolithic reactor packings is significantly improved catalyst utilization without any pressure drop penalty. Literature values for the effectiveness of commercial catalyst pellets of about ⅛ inch diameter indicate that only about 50–70% of the catalyst volume is effectively available for the conversion reaction. Smaller pellet sizes can improve the level of catalyst use, and can also better facilitate styrene out-diffusion from the catalyst inside to reduce undesirable styrene polymerization reactions. However, as previously noted, smaller pellet sizes undesirably increase reactor pressure drop.

These differences in performance characteristics between monolithic and pelletized catalyst beds can be better understood from Table I below. Table I lists modeled pressure drop and characteristic heat/mass transfer data for two monolithic catalyst beds and a ⅛-inch bead catalyst bed of substantially the same void fraction. The data presented are for a feed stream moving at a superficial gas linear flow velocity of about 6.8 m/s, a flow velocity not atypical of a commercial radial flow reactor considered as if operated in an axial flow mode.

The characteristic heat/mass transfer dimension of each of the catalysts shown in Table I is taken to be the smallest catalyst cross-section or dimension, reported in millimeters. The heat/mass transfer dimension is a critical number determining how fast reactant molecules can move into and out of the catalyst bulk, (the mass transfer process), and how fast heat can be taken up or given off by the catalyst bulk (the heat transfer process). Generally, the mass and heat transfer rates are inversely proportional to this characteristic dimension.

TABLE 1

Catalyst Flow & Mass Transfer Characteristics

| Packed bed properties | Monolithic Catalyst #1 | Monolithic Catalyst #2 | Pellet Bed Catalyst |
|---|---|---|---|
| Void fraction | 0.5 | 0.5 | 0.5 |
| Smallest Catalyst Thickness, (mm) | 1 | 0.5 | 1/8" (bead diameter) |
| Honeycomb cell density (cpsi) | 55 | 220 | N/A |
| Pressure drop (bar/m) | 0.021 | 0.085 | 0.437 |
| Characteristic mass/heat transfer dimension (mm) | 1 | 0.5 | 3.2 |

As shown by the data in Table I, typical pressure drops across monolithic catalysts of 220 and 55 channels per square inch (cpsi) of honeycomb cross-section (i.e., the cross-section perpendicular to the channel axes), are about 0.085 and 0.02 bar per meter (bar/m) of flowpath length, respectively. In contrast, the pressure drop cross a conventional bead or pellet catalyst bed at the same void fraction is about 0.44 bar/meter, a level about 20 times that of the 55 cpsi honeycomb catalyst.

In the case of the monolithic catalysts the characteristic mass/heat transfer dimension is in the range of 0.5–1.0 mm, corresponding to the thickness of the honeycomb catalyst wall. For the bead catalyst the heat/mass transfer dimension is about 3.2 mm, corresponding to the bead diameter. Thus both low pressure drop and enhanced heat/mass transfer are characteristic of the honeycomb catalyst.

While monolithic honeycomb catalysts may be provided over a very broad range of monolith sizes, cell densities, and channel wall thicknesses, it will be found that best conversion efficiencies are secured over a relatively narrow range of geometries. Honeycomb cell densities will typically range between 10–900 channels per square inch (cpsi) of honeycomb cross-section, more preferably between 150–200 cpsi. Channel walls in these honeycombs will be about 0.1–5 mm in thickness, more preferably about 0.3–2 mm in thickness.

To control reactor inlet pressure and catalyst bed pressure drop, the honeycombs will have open-front void fractions (open frontal areas) of at least about 0.1 (i.e, 10% of the area of the honeycomb cross-section will consist of open channel area). More preferably, the honeycomb void fractions will be in the range of about 0.3 to 0.8, with void fractions above about 0.9 being impractical from the standpoint of honeycomb strength.

As previously noted, the method of the invention can be utilized for the dehydrogenation of a variety of alkyl aromatic compounds, but is particularly advantageous for the conversion of ethylbenzene to styrene. For that purpose, the reactant stream being processed can comprise from as little as 20% to substantially 100% of ethylbenzene by volume, but more typically will consist of a mixture of ethylbenzene and steam ($H_2O$ vapor). Suitable steam-ethylbenzene mixtures have steam:ethylbenzene molar ratios in the range of 0.1:1 to 40:1.

Prior to conveying such a reactant stream through a honeycomb catalyst bed in a dehydrogenation reactor or honeycomb reactor stage, the stream must be heated to a temperature at which conversion within the honeycomb catalyst can effectively occur. For the first-stage dehydrogenation processing of an ethylbenzene reactant stream, the effective temperature for honeycomb dehydrogenation catalysts will normally be in the range of about 400 to 750° C.

The pressures and flow rates of the reactant stream through the honeycomb catalyst stages will also be set at values at which efficient honeycomb dehydrogenation can occur. In the case of ethylbenzene conversion to styrene, for example, reactant stream pressures in the range of about 0.01 to 3.0 bar within the honeycombs, and liquid hour space velocities through the honeycombs in the range of about 0.1/hour to 30/hour, provide good conversion efficiencies with honeycomb geometries such as hereinabove described. Such geometries permit the use of superficial linear reactant stream flow velocities as low as 0.5 meters/second and as high as 50 meters/second through the honeycomb channels within the ranges of space velocity and reactant stream pressure described.

Radial flow dehydrogenation reactors are known to offer the advantage of lowering pressure drop by reducing gas linear velocity through the catalyst bed. A commercial radial flow reactor having a catalyst bed made up of catalyst pellets and having a cross-sectional area, for example, of 12.6 square meters might run at a reactor pressure on the order of 0.7 bar, a pressure drop of 0.1 bar, a temperature of 870° K., and a reactant stream mass flow rate of 15 kg/sec which is equivalent to a superficial linear flow velocity of 6.8 meters/sec for a reactor of this cross-sectional area.

However, as is evident from the given catalyst bed size, such reactors are not space efficient, do not allow for easy control of reactor temperature profile, and present difficulties in the loading and unloading of the catalyst. Also, they offer catalyst mass and heat transfer efficiencies not significantly different from those of conventional pellet bed axial flow reactors.

An example of a monolithic reactor incorporating honeycomb packing provided in accordance with the invention is shown in FIG. 1 of the drawing. The schematic elevational view of FIG. 1, not presented in true proportion or to scale, shows a cross-section of a typical monolith reactor with its main included components, and indicates its mode of operation.

Referring more specifically to FIG. 1, reactor 8 includes a reactor chamber 10 within which are disposed first or upstream monolithic (honeycomb) dehydrogenation catalyst bed 12 and second or downstream monolithic dehydrogenation catalyst bed 14. In this illustration each bed is formed of a single large honeycomb catalyst, although each bed could equivalently be formed of multiple smaller blocks of monolithic honeycomb catalysts assembled form a catalyst bed of any required size. These catalysts together form the monolithic packing of the reactor.

A reactant stream containing a reactant to be treated for the purpose of dehydrogenation, such as a stream comprising ethylbenzene represented in FIG. 1 by arrow 20, is introduced into chamber 10 via chamber inlet 16 and flows through the reactor in the arrow direction until it exits the reactor via outlet 18 as a product stream represented by arrow 22. The direction of the arrows 20 and 22 defines the flow axis through the reactor, which lies generally parallel with the honeycomb channels represented by channels 12a and 14a traversing the lengths monolithic catalysts 12 and 14, respectively.

Reaction chamber 10 further includes heating means 30, which in this case is a steam heating coil into which a high temperature supply of steam indicated by arrow 32 is introduced. This steam heats coil 30 to re-heat the reactant stream after it has passed through first monolithic catalyst 12 and prior to its introduction into second or downstream monolithic catalyst 14. After transferring its heat to the reactant stream, the cooled or condensed steam exits heating coil 30 as represented by arrow 34.

The heating means utilized to add heat energy to the reactant stream is not critical. Alternative means for achieving the same result could include electrical heating elements, systems for conveying other heat transfer fluids through the section of the reaction chamber separating the monolithic catalysts, or systems for releasing steam or other hot gases directly into the reactant stream at that point in the reactor. Since steam is an effective reactive and diluting additive for carrying out reactions such as the dehydrogenation of ethylbenzene, the release of steam into the reactant stream between the adjacent monolithic catalysts can be a cost- and space-efficient method for operating reactors of this kind for the dehydrogenation of ethylbenzene to styrene.

It is the use of two or more beds formed of monolithic catalysts of appropriate lengths and cell densities within the reactor vessel that makes it possible to add heat or steam into the reactant stream at points best suited for enhancing the specificity and yield of the particular dehydrogenation reaction being supported. The resulting improvements in reactor temperature profile control will extend catalyst lifetime and catalyst utilization as well as enhance reactant conversion and product yield.

As will be appreciated from the foregoing description, the monolith reactor illustrated in FIG. 1 can be used as a stand-alone reactor vessel, or it can be used to retrofit an existing reactor apparatus. The particular use selected will of course depend on the particular plant process scheme to be employed.

When compared to radial flow reactors, honeycomb monolith reactors such as herein described not only simplify reactor design but also better utilize reactor space and improve flow distribution. These advantages can be realized in many different ways depending on the specific processing configuration to be used, but in a multi-stage reactor system, the monolith reactor is best used for the front-stage conversion section.

In the case of two-stage radial flow reactor systems for ethylbenzene dehydrogenation, for example, a monolith reactor is particularly useful as a first stage converter upgrade to replace the first radial stage in the system. The resulting systems, which can offer significantly improved overall performance, employ the axial flow monolithic reactor to supply the second stage or downstream radial flow reactor with an intermediate reactant feed stream of lower unreacted ethylbenzene content.

Figure 2:
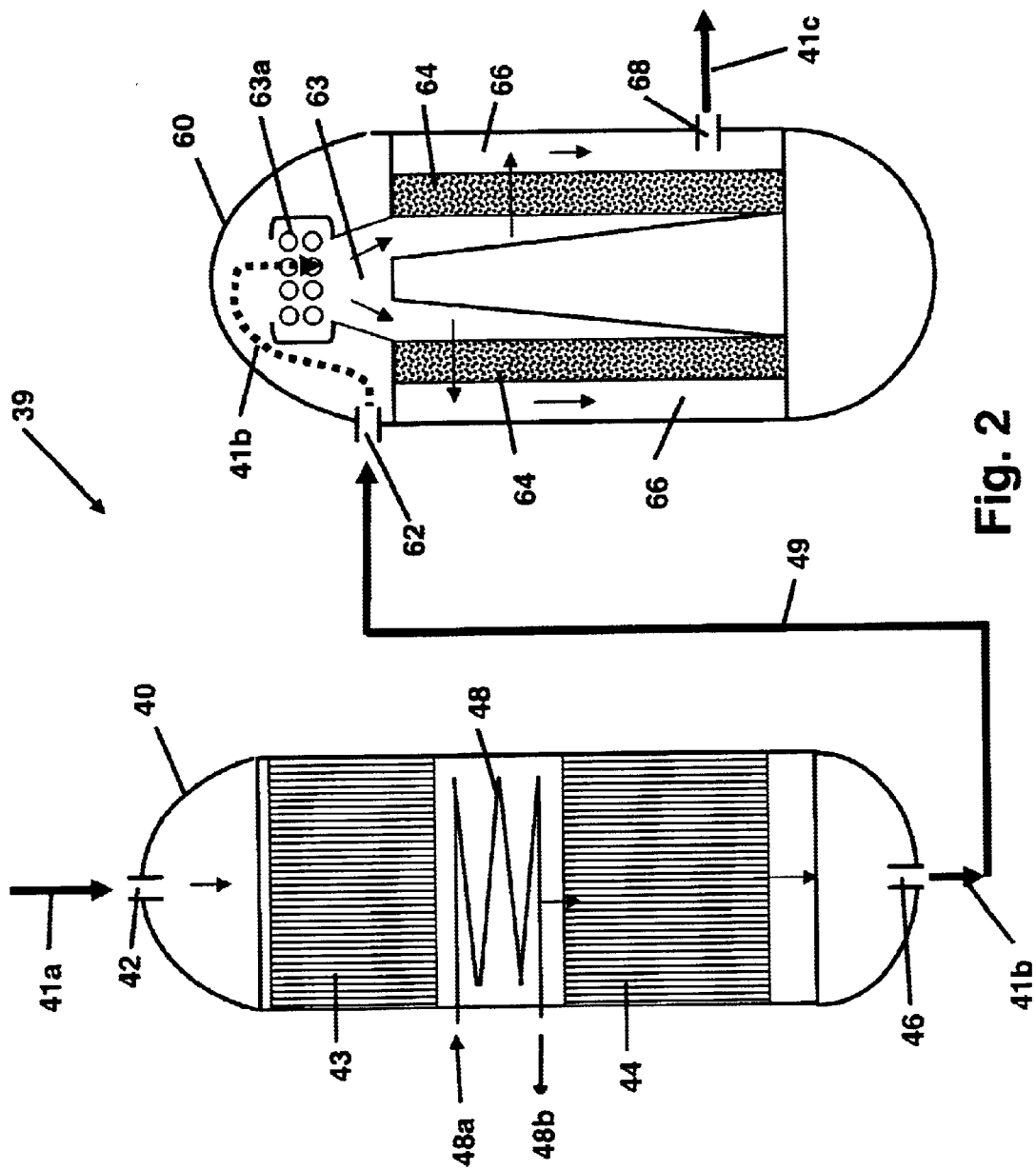
FIG. 2 is a schematic elevational view of a two-stage dehydrogenation reactor comprising honeycomb monolith and radial flow stages in accordance with the invention.

An example of a reactor system following this design is schematically illustrated in FIG. 2 of the drawings. As shown in the cross-sectional elevational view of FIG. 2, although not in true proportion or to scale, reactor system 39 includes a first stage monolithic packing reactor 40 and a second stage radial flow reactor 60. These reactors are arranged so that a reactant stream entering reactor 40 at inlet 42, for example a stream indicated by arrow 41a of a reactant such as ethylbenzene to be dehydrogenated, traverses monoliths 43 and 44 within reactor 40 in the direction of the arrow, and exits the reactor enclosure at outlet 46 as a partially dehydrogenated reactant stream 41b. Desirably, the reactant stream is heated within the reactor by steam heating coil 48 supplied with steam as indicated by arrows 48a and 48b.

Partially dehydrogenated reactant stream 41b is next conveyed via conduit 49 to inlet 62 of radial flow reactor 60, where it is first re-heated by an in situ heat exchanger 63a and then supplied to central inlet section 63 of the reactor for distribution. Stream 41b is then forced outwardly through radial flow catalyst bed 64 into circumferential reactor outlet section 66 as a dehydrogenated product. This product is then collected and discharged from reactor 60 via reaction chamber outlet 68 as dehydrogenated reactant stream 41c.

One advantage of substituting the monolithic for the radial flow stage in this reactor design is that, even when the combined volume of the monolithic packings in the axial flow reactor remains the same as the volume of the packed bed catalyst in the replaced radial stage, nearly 50% of the reactor space is saved. This extra space can be used to install heating means between the monolithic packing elements of the axial flow reactor, with two or even three internal heat exchangers imparting significant performance improvements to the system. Kinetics modeling indicates that the resulting improvements in reactor temperature profile control, together with improved catalyst utilization, can increase one-pass ethylbenzene conversion rates by more than 15% under equivalent reaction conditions. Higher feed stream throughputs are also possible.

The value of these improvements can be better understood from a more detailed study of the behavior of candidate reactor designs. Performance data derived from kinetic modeling for a typical adiabatic two-stage radial flow reactor are reported in Table 2 below. The data reported are for a two-stage ethylbenzene dehydrogenation reactor of approximately 250,000 tons/year ethylbenzene processing capacity. The reactant stream modeled is An 8.8:1 mole ratio steam:ethylbenzene mixture flowing through the catalyst beds within the reactor at a liquid hour space velocity (LHSV) of 0.64 $hr^{-1}$.

Included in Table 2 for each of the two radial flow reactor stages are the inlet and outlet pressures of the reactant stream, in bars, the temperatures of the reactant stream at each inlet and outlet, in degrees K., the LHSV flow rates through the two stages, and the cumulative ethylbenzene conversion, as fractions of the amount of EB in the initial feed stream.

TABLE 2

Radial Flow Reactor Performance

| Performance Data | Radial Stage 1 | Radial Stage 2 |
| --- | --- | --- |
| Inlet pressure, bar | 0.562 | 0.479 |
| Outlet pressure, bar | 0.514 | 0.397 |
| Inlet temperature, K | 895 | 895 |
| Outlet temperature, K | 818 | 848 |
| LHSV, 1/h | 0.64 | 0.64 |
| EB conversion fraction | 0.392 | 0.633 |

As can be seen from the data in Table 2, under these particular operating conditions the ethylbenzene conversion rate through the first reactor stage is 0.39, with the reactant temperature dropping rapidly from 895° K. to 818° K. as the reacting gases pass through the catalyst bed. This large temperature drop clearly indicates that not all of the first stage catalyst bed efficiently contributes to the ethylbenzene conversion, since the catalyst conversion efficiency drops rapidly with temperature. The conclusion to be drawn is that increasing the catalyst content in this reactor stage would be much less effective to increase conversion efficiency than would improving the temperature uniformity within the reactor.

This can be effectively accomplished through a replacement of the first stage reactor with an axial flow monolith reactor as illustrated in FIG. 2 of the drawing. In the redesigned reactor the volume of the catalyst bed is not increased but the space saved from the elimination of the radial flow distributor is used to install a single internal heat exchanger located between two monolithic honeycomb catalyst beds of substantially equal size.

Data for the reaction performance of a hybrid axial/radial flow reactor system such as shown in FIG. 2 of the drawing are reported in Table 3 below. The results are calculated for the same initial reactant composition, temperature, and space velocity employed to calculate the data in Table 2. Included in Table 3 for each of the two reactor stages are the inlet and outlet pressures of the reactant stream, in bars, the temperatures of the reactant stream at each inlet and outlet, in degrees K., the LHSV flow rates through the two stages, and the cumulative ethylbenzene conversion rates, as fractions of the amount of ethylbenzene in the initial feed stream. Also included in Table 3 is a breakdown showing the inlet and outlet temperatures, pressures and conversion rates for each of the two sections of the monolith reactor stage.

TABLE 3

Radial-Axial (Honeycomb) Reactor Performance

| | Axial Reactor Stage | | Radial Reactor Stage |
| --- | --- | --- | --- |
| Performance Data | Monolith Zone 1 | Monolith Zone 2 | Radial Catalyst Bed |
| Inlet pressure, bar | 0.562 | 0.538 | 0.479 |
| Outlet pressure, bar | 0.54 | 0.51 | 0.40 |
| Inlet temperature, K | 895 | 895 | 895 |
| Outlet temperature, K | 825.94 | 855.92 | 862.18 |
| LHSV, 1/h | 1.28 | 1.28 | 0.64 |
| EB conversion fraction | 0.35 | 0.56 | 0.73 |

As the data presented in Table 3 indicates, under the same overall space velocity (throughput), inlet temperature, and catalyst activity, the final one-pass ethylbenzene conversion effected by the hybrid reactor system increases to 0.73 from the base case of 0.633 for the two stage radial reactor. These improvements are attributed to the combination of better catalyst utilization and better reactor temperature control in the hybrid reactor system.

Still another advantage of axial flow reactors employing monolithic packings is the fact that they can be operated at significantly higher throughputs than reactors incorporating conventional packings. This result is due to the high catalyst utilization efficiencies and reduced pressure drops encountered in honeycomb reactor stages.

The data in Table 4 below are for a hybrid reactor operated under conditions similar to those reported in Table 3, except that reactor throughput is increased by increasing the space velocity of the reactant stream by about 25%. The resulting one-pass ethylbenzene conversion efficiencies are still significantly higher than for the case of the two stage radial reactor, and the yearly styrene production capacity of the reactor increases from approximately 250,000 tons per year to about 312,000 tons per year.

TABLE 4

Hybrid Reactor - High Throughput Efficiency

| | Axial Reactor Stage | | |
| --- | --- | --- | --- |
| Performance Data | Monolith Zone 1 | Monolith Zone 2 | Radial Reactor Stage Radial Catalyst Bed |
| Inlet pressure, bar | 0.562 | 0.538 | 0.479 |
| Outlet pressure, bar | 0.54 | 0.51 | 0.40 |
| Inlet temperature, K | 895 | 895 | 895 |
| Outlet temperature, K | 825.94 | 855.92 | 862.18 |
| LHSV, 1/h | 1.6 | 1.6 | 0.8 |
| EB conversion fraction | 0.341 | 0.534 | 0.703 |

The foregoing data confirm that substantial performance advantages can be secured through the use of monolithic honeycomb reactors or reactor stages to improve catalyst usage and better control reactor temperature profiles in ethylbenzene and similar endothermic dehydrogenation reactions of the kind herein described of course, the particular examples set forth above are merely illustrative of the variations in design and practice that may be resorted to by those skilled in the art within the scope of the appended claims.

We claim:

1. An axial flow dehydrogenation reactor comprising:
   a reaction chamber having an inlet and an outlet and containing two or more catalyst beds including an upstream bed and a downstream bed disposed in series along a flow axis traversing the chamber from an upstream to a downstream direction between the inlet and the outlet;
   each catalyst bed being formed of one or more monolithic dehydrogenation catalysts each catalyst incorporating a plurality of open-ended honeycomb channels traversing the catalyst from the upstream to the downstream direction for treating a heated vapor stream containing a hydrogen-containing reactant to at least partially convert the reactant to a dehydrogenated product;

the catalyst beds being separated by steam or electrical heating means disposed therebetween for re-heating the vapor stream after traverse through the upstream bed and prior to traverse through the downstream bed.

2. An axial flow dehydrogenation reactor in accordance with claim 1 having a reactor diameter:reactor length ratio in the range of 1:1 to 1:30.

3. An axial flow dehydrogenation reactor in accordance with claim 1 wherein the honeycomb channels in the monolithic dehydrogenation catalysts are bounded by channel walls having thicknesses in the range of 0.1 to 5 mm.

4. An axial flow dehydrogenation reactor in accordance with claim 3 wherein the channel walls have thicknesses in the range of 0.3 to 2 mm.

5. An axial flow dehydrogenation reactor in accordance with claim 1 wherein the monolithic dehydrogenation catalysts have honeycomb cell densities in the range of 10 to 900 cells per square inch of honeycomb cross-section.

6. An axial flow dehydrogenation reactor in accordance with claim 5 wherein the honeycomb cell densities are in the range of 150–200 cells per square inch of honeycomb cross-section.

7. An axial flow dehydrogenation reactor in accordance with claim 1 wherein the monolithic dehydrogenation catalysts have open-front void fractions in the range of 0.1 to 0.9.

8. An-axial flow dehydrogenation reactor in accordance with claim 7 wherein the monolithic dehydrogenation catalysts have open-front void fractions in the range of 0.3 to 0.8.

9. A multiple-stage dehydrogenation reactor comprising:

a first reactor stage incorporating a first reaction chamber containing at least one catalyst bed formed of one or more monolithic dehydrogenation catalysts, each catalyst having an inlet face, an outlet face, and a plurality of open-ended honeycomb channels traversing the catalyst in a downstream direction from the inlet face toward the outlet face;

a first chamber inlet for supplying a vapor stream comprising a hydrogen-containing reactant to the monolithic catalyst for conversion of the reactant to a partially dehydrogenated product;

a first chamber outlet for discharging the vapor stream from the chamber;

a second reactor stage positioned in the downstream direction from the first reactor stage, the second stage including a second chamber containing a second dehydrogenation catalyst and having a second chamber inlet for admitting the partially dehydrogenated product into the second chamber for treatment by the second catalyst; and heating means disposed between and connected to the first chamber outlet and the second chamber inlet for heating the vapor stream discharged from the first chamber outlet prior to entry into the second chamber inlet, the vapor stream being heated to a temperature at least sufficient to permit further catalytic dehydrogenation of the hydrogen-containing reactant present in the partially hydrogenated vapor stream upon contact with the second dehydrogenation catalyst disposed in the second reactor stage.

10. A multiple-stage dehydrogenation reactor in accordance with claim 9 wherein the second reactor stage is a radial flow reactor stage.

11. A multiple-stage dehydrogenation reactor in accordance with claim 9 wherein the first reactor stage incorporates at least two catalyst beds formed of monolithic dehydrogenation catalysts.

12. A multiple-stage dehydrogenation reactor in accordance with claim 11 wherein steam or electrical heating means for adding heat to the reactant stream are disposed between the catalyst beds.

13. A multiple-stage dehydrogenation reactor in accordance with claim 9 wherein the second dehydrogenation catalyst is a monolithic honeycomb catalyst.

14. A multiple-stage dehydrogenation reactor in accordance with claim 9 wherein the second dehydrogenation catalyst is a pelletized catalyst.

15. A method for treating a reactant feed stream to dehydrogenate a hydrogen-containing reactant present therein which comprises the steps of:

heating the reactant stream to a first dehydrogenation reaction temperature and thereafter conveying the stream through a first dehydrogenation reactor containing at least one catalyst bed of monolithic honeycomb dehydrogenation catalysts to effect at least partial dehydrogenation of the reactant, thus to produce a partially dehydrogenated intermediate stream;

heating the intermediate stream to a second dehydrogenation reaction temperature; and conveying the intermediate stream through a second dehydrogenation reactor containing at least one catalyst bed of a second dehydrogenation catalyst to effect further dehydrogenation of the intermediate stream, thus to produce a dehydrogenated product stream.

16. A method in accordance with claim 15 wherein the reactant is an alkyl aromatic compound.

17. A method in accordance with claim 15 wherein the reactant is ethylbenzene.

18. A method in accordance with claim 17 wherein the reactant stream comprises 20 to 100% ethylbenzene by volume.

19. A method in accordance with claim 17 wherein the reactant stream comprises steam and ethylbenzene in a steam:ethylbenzene molar ratio in the range of 0.1:1 to 40:1.

20. A method in accordance with claim 17 wherein the reactant is heated to a first dehydrogenation reaction temperature in the range of 400 to 750° C.

21. A method in accordance with claim 17 wherein the reactant stream is conveyed through the first dehydrogenation reactor at a liquid hourly space velocity in the range of 0.1/hour to 30/hour.

22. A method in accordance with claim 17 wherein the absolute pressure of the reactant stream within the first dehydrogenation reactor is in the range of about 0.01 to 3.0 bar.

23. A method in accordance with claim 17 wherein the reactant stream is conveyed through the first reactor at a superficial linear velocity in the range of about 0.5–50 meters/second.

24. A method in accordance with claim 15 wherein the bed of the second dehydrogenation catalyst is formed of one or more monolithic honeycomb catalysts.

25. A method in accordance with claim 24 wherein the second dehydrogenation catalyst bed is disposed in an axial flow dehydrogenation reactor.

26. A method in accordance with claim 15 wherein the second dehydrogenation catalyst bed a low-pressure-drop bed of dehydrogenation catalyst beads or pellets.

27. A method in accordance with claim 26 wherein the second dehydrogenation catalyst bed is a catalyst bed disposed in a radial flow dehydrogenation reactor.

* * * * *